(12) United States Patent
Mechaly et al.

(10) Patent No.: US 10,882,899 B2
(45) Date of Patent: Jan. 5, 2021

(54) **ANTI *FRANCISELLA TULARENSIS* (FT) ANTIBODIES**

(71) Applicant: The Israel Institute of Biological Research (IIBR), Ness-Ziona (IL)

(72) Inventors: Adva Mechaly, Ness Ziona (IL); Ofer Cohen, Netaim (IL); Ohad Mazor, Shoham (IL)

(73) Assignee: THE ISRAEL INSTITUTE OF BIOLOGICAL RESEARCH (IIBR), Ness-Ziona (IL)

( * ) Notice: Subject to any disclaimer, the term of this patent is extended or adjusted under 35 U.S.C. 154(b) by 0 days.

(21) Appl. No.: 16/503,211

(22) Filed: Jul. 3, 2019

(65) Prior Publication Data

US 2020/0010535 A1   Jan. 9, 2020

(30) Foreign Application Priority Data

Jul. 4, 2018   (IL) .......................................... 260412

(51) Int. Cl.
*C07K 16/12*   (2006.01)
*G01N 33/569*   (2006.01)
*A61K 45/06*   (2006.01)

(52) U.S. Cl.
CPC .... *C07K 16/1203* (2013.01); *G01N 33/56911* (2013.01); *A61K 45/06* (2013.01); *C07K 2317/565* (2013.01); *C07K 2317/622* (2013.01); *C07K 2317/92* (2013.01); *G01N 2333/195* (2013.01)

(58) Field of Classification Search
None
See application file for complete search history.

(56) References Cited

U.S. PATENT DOCUMENTS

2010/0021470 A1*   1/2010   Lanzavecchia ........ C07K 16/00
                                                                424/141.1

FOREIGN PATENT DOCUMENTS

WO   2005/026732 A1   3/2005

OTHER PUBLICATIONS

Greenspan et al. 1999 (Defining epitopes: Its not as easy as it seems; Nature Biotechnology, 17:936-937) (Year: 1999).*
Rudikoff et al. 1982 (Single amino acid substitution altering antigen-binding specificity; PNAS, USA, 79(6):1979-1983) (Year: 1982).*
Fulop et al. 1991 (Production and characterization of monoclonal antibodies directed against the lipopolysaccharide of *Francisella tularensis*; Journal of Clinical Microbiology; 29(7):1407-1412) (Year: 1991).*
Ahmad et al. 2012 (scFv Antibody: Principles and Clinical Application; Clinical and Developmental Immunology; vol. 2012, Article ID 980250, 15 pages doi:10.1155/2012/980250). (Year: 2012).*
Bar-On, L. et al . Protection of vaccinated mice against pneumonic tularemia is associated with an early memory sentinel-response in the lung. Vaccine 2017, 35, 7001-7009.
Bina, X. R. et al . Construction of a bioluminescence reporter plasmid for francisella tularensis. Plasmid 2010, 64, 156-161.
Bitsaktsis, C. et al . In vivo mechanisms involved in enhanced protection utilizing an fc receptor-targeted mucosal vaccine platform in a bacterial vaccine and challenge model. Infect Immun 2015, 83, 77-89.
Boisset, S. et al . New therapeutic approaches for treatment of tularaemia: A review. Front Cell Infect Microbiol. 2014, 4, 40.
Dennis, D. T. et al . Tularemia as a biological weapon: Medical and public health management. JAMA 2001, 285, 2763-2773.
Duffy, E. B. et al . Fcgammar mediates tlr2- and syk-dependent nlrp3 inflammasome activation by inactivated francisella tularensis lvs immune complexes. J Leukoc Biol 2016, 100, 1335-1347.
Evans, M. E. et al. Tularemia: A 30-year experience with 88 cases. Medicine (Baltimore) 1985, 64, 251-269.
Fulop, M. et al. Role of antibody to lipopolysaccharide in protection against low- and highvirulence strains of Francisella tularensis . Vaccine , 2001, 19(31), 4465-4472.
Geier, H. and Celli, J. Phagocytic receptors dictate phagosomal escape and intracellular proliferation of francisella tularensis. Infect Immun 2011, 79, 2204-2214.
Gunn, J. S. and Ernst, R. K. The Structure and Function of Francisella Lipopolysaccharide. Ann N Y Acad Sci. 2007, 1105, 202-218.
Kirimanjeswara, G. S. et al . Prophylactic and therapeutic use of antibodies for protection against respiratory infection with francisella tularensis. J Immunol 2007, 179, 532-539.
Kirimanjeswara, G. S. et al . Humoral and cell-mediated immunity to the intracellular pathogen francisella tularensis. Immunol Rev 2008, 225, 244-255.
Kosker, M. et al . A case of oculoglandular tularemia resistant to medical treatment. Scand J Infect Dis 2013, 45, 725-727.
Krocova, Z. et al . Innate immune recognition: Implications for the interaction of francisella tularensis with the host immune system. Front Cell Infect Microbiol 2017, 7, 446.
Mara-Koosham, G. et al . Antibodies contribute to effective vaccination against respiratory infection by type a francisella tularensis strains. Infect Immun 2011, 79, 1770-1778.

(Continued)

*Primary Examiner* — Mary Maille Lyons
(74) *Attorney, Agent, or Firm* — Browdy and Neimark, PLLC

(57) ABSTRACT

An isolated monoclonal antibody or antigen-binding fragment thereof binds to *F. tularensis* lipopolysaccharide (Ft LPS). The antibody preferably lacks an Fc region or has an impaired Fc-region. The antibody may be formulated into a pharmaceutical composition along with a pharmaceutically acceptable carrier, excipient or diluent. It may be provided in a kit with means for detection of the antibody and instructions for use. A therapeutically effective amount of such an antibody can be used for prophylaxis, treatment or amelioration of Ft infection and for inhibiting Ft uptake by cells in a subject. The antibody can also be used to detect Ft infection. Also disclosed is an isolated nucleic acid molecule encoding the antibody, an expression vector having the isolated nucleic acid molecule, and a host cell transfected with such an expression vector.

8 Claims, 3 Drawing Sheets
Specification includes a Sequence Listing.

(56) References Cited

OTHER PUBLICATIONS

Mechaly, A. et al. A biolayer interferometry-based assay for rapid and highly sensitive detection of biowarfare agents. Anal Biochem 2016, 506, 22-27.

Mechaly, A. et al. Novel phage display-derived anti-abrin antibodies confer post-exposure protection against abrin intoxication. Toxins (Basel) 2018, 10, 80.

Noy-Porat, T. et al. Isolation of anti-ricin protective antibodies exhibiting high affinity from immunized non-human primates. Toxins (Basel) 2016, 8, 64.

Okan, N. A. and Kasper, D. L. The atypical lipopolysaccharide of Francisella. Carbohydr Res. 2013, 378, 79-83.

Phillips, N. J. et al. Novel modification of lipid a of francisella tularensis. Infect Immun 2004, 72, 5340-5348.

Roche, M. I. et al. Characterization of monoclonal antibodies to terminal and internal oantigen epitopes of francisella tularensis lipopolysaccharide. Hybridoma (Larchmt) 2011, 30, 19-28.

Rosenfeld, R. et al. Isolation and chimerization of a highly neutralizing antibody conferring passive protection against lethal bacillus anthracis infection. PLoS One Jul. 2009, 4, Issue 7, e6351.

Rotem, S. et al. Consequences of delayed ciprofloxacin and doxycycline treatment regimens against francisella tularensis airway infection. Antimicrob Agents Chemother 2012, 56, 5406-5408.

Savitt, A. G. et al. Francisella tularensis infection-derived monoclonal antibodies provide detection, protection, and therapy. Clin Vaccine Immunol 2009, 16, 414-422.

Zaide, G. et al. Identification and characterization of novel and potent transcription promoters of francisella tularensis. Appl Environ Microbiol 2011, 77, 1608-1618.

* cited by examiner

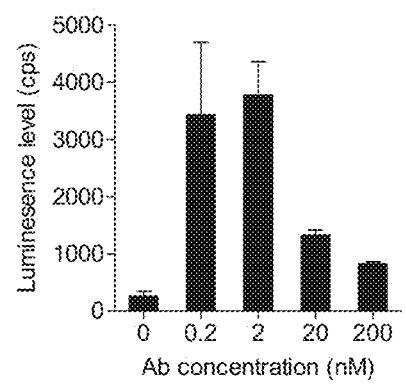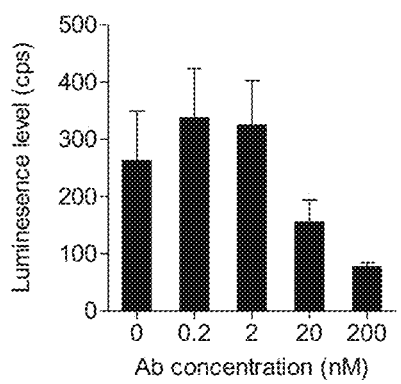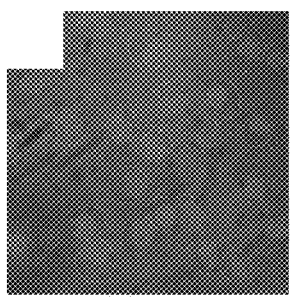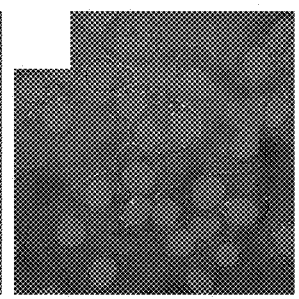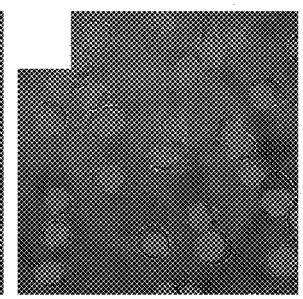

ANTI FRANCISELLA TULARENSIS (FT) ANTIBODIES

The Sequence Listing in ASCII text file format of 5,839 bytes in size, created on Jul. 3, 2019, with the file name "2019-07-03Sequence_Listing-MECHALY1," filed in the U.S. Patent and Trademark Office on even date herewith, is hereby incorporated herein by reference.

TECHNOLOGICAL FIELD

This invention generally relates to anti-*Francisella tularensis* (Ft) lipopolysaccharide (LPS) antibodies for use in detection and treatment of Ft infection.

BACKGROUND ART

References considered to be relevant as background to the presently disclosed subject matter are listed below:

Bar-On, L. et al. Protection of vaccinated mice against pneumonic tularemia is associated with an early memory sentinel-response in the lung. *Vaccine* 2017, 35, 7001-7009.

Bina, X. R. et al. Construction of a bioluminescence reporter plasmid for *Francisella tularensis*. *Plasmid* 2010, 64, 156-161.

Bitsaktsis, C. et al. In vivo mechanisms involved in enhanced protection utilizing an fc receptor-targeted mucosal vaccine platform in a bacterial vaccine and challenge model. *Infect Immun* 2015, 83, 77-89.

Boisset, S. et al. New therapeutic approaches for treatment of tularaemia: A review. *Front Cell Infect Microbiol.* 2014, 4, 40.

Dennis, D. T. et al. Tularemia as a biological weapon: Medical and public health management. *JAMA* 2001, 285, 2763-2773.

Duffy, E. B. et al. Fcgammar mediates tlr2- and syk-dependent nlrp3 inflammasome activation by inactivated *Francisella tularensis* lvs immune complexes. *J Leukoc Biol* 2016, 100, 1335-1347.

Evans, M. E. et al. Tularemia: A 30-year experience with 88 cases. *Medicine* (Baltimore) 1985, 64, 251-269.

Fulop, M. et al. Role of antibody to lipopolysaccharide in protection against low- and high-virulence strains of *Francisella tularensis*. *Vaccine*, 2001, 19(31), 4465-4472.

Geier, H. and Celli, J. Phagocytic receptors dictate phagosomal escape and intracellular proliferation of *Francisella tularensis*. *Infect Immun* 2011, 79, 2204-2214.

Gunn, J. S. and Ernst, R. K. The Structure and Function of *Francisella* Lipopolysaccharide. *Ann N Y Acad Sci.* 2007, 1105, 202-218.

Kirimanjeswara, G. S. et al. Prophylactic and therapeutic use of antibodies for protection against respiratory infection with *Francisella tularensis*. *J Immunol* 2007, 179, 532-539.

Kirimanjeswara, G. S. et al. Humoral and cell-mediated immunity to the intracellular pathogen *Francisella tularensis*. *Immunol Rev* 2008, 225, 244-255.

Kosker, M. et al. A case of oculoglandular tularemia resistant to medical treatment. *Scand J Infect Dis* 2013, 45, 725-727.

Krocova, Z. et al. Innate immune recognition: Implications for the interaction of *Francisella tularensis* with the host immune system. *Front Cell Infect Microbiol* 2017, 7, 446.

Mara-Koosham, G. et al. Antibodies contribute to effective vaccination against respiratory infection by type a *Francisella tularensis* strains. *Infect Immun* 2011, 79, 1770-1778.

Mechaly, A. et al. A biolayer interferometry-based assay for rapid and highly sensitive detection of biowarfare agents. *Anal Biochem* 2016, 506, 22-27.

Mechaly, A. et al. Novel phage display-derived anti-abrin antibodies confer post-exposure protection against abrin intoxication. *Toxins* (Basel) 2018, 10.

Noy-Porat, T. et al. Isolation of anti-ricin protective antibodies exhibiting high affinity from immunized non-human primates. *Toxins* (Basel) 2016, 8.

Okan, N. A. and Kasper, D. L. The atypical lipopolysaccharide of *Francisella*. *Carbohydr Res.* 2013, 378, 79-83.

Phillips, N. J. et al. Novel modification of lipid a of *Francisella tularensis*. *Infect Immun* 2004, 72, 5340-5348.

Roche, M. I. et al. Characterization of monoclonal antibodies to terminal and internal o-antigen epitopes of *Francisella tularensis* lipopolysaccharide. *Hybridoma* (Larchmt) 2011, 30, 19-28.

Rosenfeld, R. et al. Isolation and chimerization of a highly neutralizing antibody conferring passive protection against lethal *Bacillus anthracis* infection. *PLoS One* 2009, 4, e6351.

Rotem, S. et al. Consequences of delayed ciprofloxacin and doxycycline treatment regimens against *Francisella tularensis* airway infection. *Antimicrob Agents Chemother* 2012, 56, 5406-5408.

Savitt, A. G. et al. *Francisella tularensis* infection-derived monoclonal antibodies provide detection, protection, and therapy. *Clin Vaccine Immunol* 2009, 16, 414-422.

Zaide, G. et al. Identification and characterization of novel and potent transcription promoters of *Francisella tularensis*. *Appl Environ Microbiol* 2011, 77, 1608-1618.

WO 2005/026732.

Acknowledgement of the above references herein is not to be inferred as meaning that these are in any way relevant to the patentability of the presently disclosed subject matter.

BACKGROUND

*Francisella tularensis* (Ft) is a virulent Gram-negative, facultative intracellular bacterium and the causative agent of lethal tularemia. Due to its high infectivity and mortality rates, Ft is classified as a category A biological warfare threat agent by the Center for Disease Control and Prevention (CDC). Tularemia is usually treatable by antibiotics, however, only few antibiotics were recommended as the treatment of choice (Dennis et al. 2001). Although there are no known natural strains of Ft that acquired antibiotic resistance, many therapeutic failures and relapses observed in infected patients were reported (Kosker et al. 2013) and about 2% mortality rates were reported for antibiotic-treated patients (Evans et al. 1985). Thus, several attempts were made to develop novel and effective treatments for tularemia (Boisset et al. 2014).

The role of antibody-mediated protection against intracellular pathogens in general and for Ft in particular has long been controversial. Indeed, several studies have shown that antibodies directed against the lipopolysaccharide (LPS) of Ft can be used for the treatment of mice infected with the live attenuated strain (LVS). However, these antibodies were much less effective in protecting mice that were infected with the virulent type A SchuS4 Ft strain (Fulop et al. 2001; Savitt et al. 2009; Kirimanjeswara et al. 2007; Mara-Koosham et al. 2011). It was also demonstrated that binding of the antibody-coated bacteria to the Fc-gamma receptor (FcγR) located on phagocytic cells such as macrophages and neutrophils is a key process needed for efficient protection against LVS (Duffy et al. 2016). On the other hand, these same cell types are the main target of Ft that utilizes several receptors, including FcγR to enter the cytosol and escape from the immune system (Krocova et al. 2017). Interestingly, this exact uptake mechanism is also being investigated as a way to enhance the uptake of inactivated Ft in order to provoke efficient immune response and as a means to create a platform for vaccination (Bitsaktsis et al. 2015).

It was previously suggested that the failure of anti-Ft antibodies to provide efficient protection against the virulent strain, although they can bind it very efficiently, is due to a complete shutdown of the inflammatory response needed for efficient antibody-mediated clearance of the bacteria (Kirimanjeswara et al. 2008). Yet, others have shown that opsonization of the SchuS4 strain using antibodies changed the intracellular fate of the bacteria and limited its ability to replicate in the cytosol (Geier and Celli 2011).

Various anti-Ft LPS antibodies were reported to date, for example as detailed in WO 2005/026732. In particular, Roche et al. describe IgG2a anti-LPS monoclonal antibodies (Mabs) specific for the O-polysaccharide (termed O-antigen or OAg) of Ft LPS. Three of the MAbs bind to immunodominant repeating internal epitopes, and one binds to a unique terminal epitope of Ft OAg.

Early and sensitive detection of Ft is highly important in order to initiate prompt life-saving antibiotic medical treatment (Rotem et al. 2012). Therefore several assays were developed aiming for sensitive and specific detection of this agent (Mechaly et al. 2016).

GENERAL DESCRIPTION

The present disclosure provides an isolated monoclonal antibody or antigen-binding fragment thereof which binds to *F. tularensis* lipopolysaccharide (Ft LPS), wherein said antibody lacks an Fc region or has an impaired Fc-region.

In some embodiments the isolated monoclonal antibody or antigen-binding fragment thereof according to the present disclosure cannot bind the Fc receptor (FcR), e.g. the Fc-gamma receptor (FcγR).

In other embodiments the isolated monoclonal antibody or antigen-binding fragment thereof according to the present disclosure binds to the O-polysaccharide (O-antigen) chain of Ft LPS.

In further embodiments the isolated monoclonal antibody or antigen-binding fragment thereof according to the present disclosure binds to the four-sugar repeats in the Ft LPS OAg chains.

In still further embodiments the binding of the isolated monoclonal antibody or antigen-binding fragment thereof according to the present disclosure to Ft LPS is characterized by a dissociation constant (Kd) smaller than $1\times10^{-7}$ 1/s ($Sec^{-1}$).

In some embodiments the isolated monoclonal antibody or antigen-binding fragment thereof according to the present disclosure inhibits Ft uptake by cells in a subject.

In certain embodiments the isolated monoclonal antibody or antigen-binding fragment thereof according to the present disclosure is a single chain variable fragment (scFv) molecule.

In various other embodiments the isolated monoclonal antibody or antigen-binding fragment thereof according to the present disclosure comprises a heavy chain complementarity determining region (CDRH) 1 denoted by SEQ ID NO. 5, CDRH2 denoted by SEQ ID NO. 6, CDRH3 denoted by SEQ ID NO. 7, and the light chain complementarity determining region (CDRL) 1 denoted by SEQ ID NO. 8, a CDRL2 denoted by SEQ ID NO. 9, and a CDRL3 denoted by SEQ ID NO. 10.

In still further embodiments the isolated monoclonal antibody or antigen-binding fragment thereof according to the present disclosure comprises a heavy chain variable region and a light chain variable region, wherein said heavy chain variable region is encoded by a nucleic acid sequence which is at least 70% identical to the nucleic acid sequence denoted by SEQ ID NO. 1 and wherein said light chain variable region is encoded by a nucleic acid sequence which is at least 70% identical to the nucleic acid sequence denoted by SEQ ID NO. 2.

In other embodiments the isolated monoclonal antibody or antigen-binding fragment thereof according to the present disclosure comprises a heavy chain variable region comprising the amino acid sequence denoted by SEQ ID NO. 3 or a variant thereof and a light chain variable region comprising the amino acid sequence denoted by SEQ ID NO. 4, or a variant thereof.

The present disclosure further provides an isolated nucleic acid molecule comprising a nucleotide sequence encoding an antibody or antigen-binding fragment thereof according to the present disclosure.

By another one of its aspects the present disclosure provides an expression vector comprising the isolated nucleic acid molecule as herein defined.

Still further the present disclosure provides a host cell transfected with the expression vector according to the present disclosure.

By yet another one of its aspects the present disclosure provides an immunoconjugate comprising the antibody or antigen-binding fragment thereof according to the present disclosure and an additional therapeutic agent.

The present disclosure further provides a pharmaceutical composition comprising as an active ingredient the isolated monoclonal antibody or antigen-binding fragment thereof according to the present disclosure or the immunoconjugate as herein defined, and a pharmaceutically acceptable carrier, excipient or diluent.

In some embodiments the pharmaceutical composition according to the present disclosure further comprises an additional therapeutic agent.

In other embodiments the additional therapeutic agent as herein defined is an antibiotic.

The present disclosure further encompasses a method of prophylaxis, treatment or amelioration of Ft infection comprising administering to a subject in need thereof a therapeutically effective amount of the isolated monoclonal antibody or antigen-binding fragment thereof, the immunoconjugate or the pharmaceutical composition according to the present disclosure.

In some embodiments the method according to the present disclosure further comprises administering to a subject in need thereof an additional therapeutic agent.

In other embodiments the method according to the present disclosure is wherein the antibody or antigen-binding fragment thereof as herein defined is administered to said subject in a single dose or in multiple doses.

In further embodiments the method according to the present disclosure is wherein the antibody or antigen-binding fragment thereof as herein defined is administered at a therapeutically effective amount of 10 µg/kg to about 50 mg/kg.

By still another one of its aspects the present disclosure provides a method of inhibiting Ft uptake by cells in a subject comprising administering to a subject in need thereof a therapeutically effective amount of the isolated monoclonal antibody or antigen-binding fragment thereof, the immunoconjugate or the pharmaceutical composition according to the present disclosure.

The present invention further provides the isolated monoclonal antibody or antigen-binding fragment thereof according to the present disclosure for use in a method of prophylaxis, treatment or amelioration of Ft infection.

Still further the present disclosure provides an isolated monoclonal antibody or antigen-binding fragment thereof which binds to *F. tularensis* LPS, wherein said antibody comprises a heavy chain complementarity determining region (CDRH) 1 denoted by SEQ ID NO. 5, CDRH2 denoted by SEQ ID NO. 6, CDRH3 denoted by SEQ ID NO. 7, and the light chain complementarity determining region (CDRL) 1 denoted by SEQ ID NO. 8, a CDRL2 denoted by SEQ ID NO. 9, and a CDRL3 denoted by SEQ ID NO. 10.

In some embodiments the isolated monoclonal antibody according to the present disclosure comprises a heavy chain variable region and a light chain variable region, wherein said heavy chain variable region is encoded by a nucleic acid sequence which is at least 70% identical to the nucleic acid sequence denoted by SEQ ID NO. 1 and wherein said light chain variable region is encoded by a nucleic acid sequence which is at least 70% identical to SEQ ID NO. 2.

In other embodiments the isolated monoclonal antibody according to the present disclosure comprises a heavy chain variable region comprising the amino acid sequence denoted by SEQ ID NO. 3 or a variant thereof and a light chain variable region comprising the amino acid sequence denoted by SEQ ID NO. 4, or a variant thereof.

Still further the present disclosure provides a method of detecting Ft LPS in a biological sample obtained from a subject, said method comprising:
 a. contacting said biological sample with the isolated monoclonal antibody or antigen-binding fragment thereof as herein defined; and
 b. detecting said isolated monoclonal antibody or any antigen-binding fragment thereof;
 wherein the presence of said isolated monoclonal antibody or any antigen-binding fragment thereof indicates the presence of Ft in said biological sample.

The present disclosure further provides a kit for detecting Ft infection comprising:
 (a) at least one isolated monoclonal antibody or antigen-binding fragment thereof as herein defined;
 (b) means for detection of said isolated monoclonal antibody; and optionally
 (c) instructions for use of said kit.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 5A is a bar graph showing the effect of TL1 (at the indicated concentrations) on Ft uptake by macrophages as measured by the intracellular luminescence level (cps). FIG. 5B is a bar graph showing the effect of TL1-scFv (at the indicated concentrations) on Ft uptake by macrophages as measured by the intracellular luminescence level (cps). FIG. 5C is a photomicrograph showing macrophages incubated with LVS in the absence of TL1. FIG. 5D is a photomicrograph showing macrophages incubated with LVS in the presence of TL1 (200 nM). FIG. 5E is a photomicrograph showing macrophages incubated with LVS in the presence of TL1-scFv (200 nM). LVS were stained using Alexa 488-conjugated rabbit anti-*F. tularensis* antibodies. Cell nuclei were stained with DAPI.

DETAILED DESCRIPTION OF EMBODIMENTS

Figure 1A:
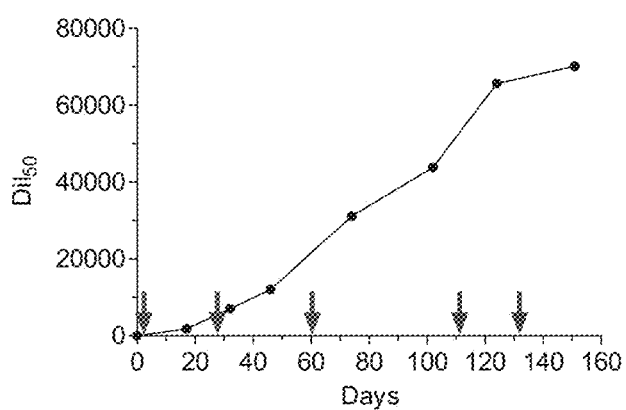
FIG. 1A is a graph showing the levels of anti-Ft polyclonal antibodies represented as the half dilution value ($Dil_{50}$) corresponding to 50% of the maximal binding of the animal serum towards the coated antigen during rabbit immunization (Days). The rabbit was injected with subcutanic injections of $1\times10^8$ colony forming units (CFU, first three arrows at the left) or $1\times10^9$ CFU (two arrows at the right). Antibody titer was determined by ELISA using LVS as the coated layer.
Figure 1B:
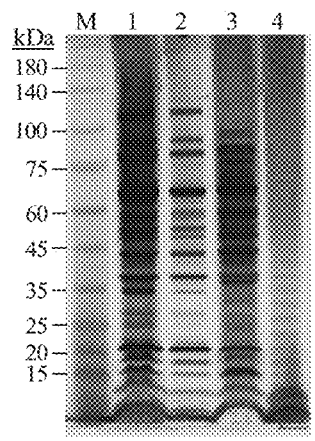
FIG. 1B shows Western blot analysis of the elicited antibodies. M—Protein size marker, 1—LVS lysate; 2—LVS-S lysate; 3—SchuS4 lysate; 4—purified LPS of LVS.

The present invention is based on the surprising finding that an anti-Ft LPS antibody that lacks the ability to bind to the FcγR successfully inhibits the entry of Ft into the host cell. Specific and high-affinity antibodies were prepared by combining an immunization methodology that promotes generation of high affinity antibodies in vivo, with efficient screening methods using phage-display libraries. Based on the identification of a high-affinity anti Ft-LPS antibody (termed herein TL1), a single chain Fv (scFv) antibody was prepared (termed herein TL1-scFv). This anti-Ft LPS scFv antibody was capable of significantly reducing bacterial uptake by cultured macrophages.

The present invention thus provides engineered antibodies that lack an Fc-region or contain a mutated Fc-region. These antibodies lack the ability to bind FcγR while retaining their pharmacokinetics parameters. Such antibodies can be used as a passive therapy for Ft infection.

Therefore, in a first of its aspects, the present invention provides an isolated monoclonal antibody or antigen-binding fragment thereof which binds to *F. tularensis* lipopolysaccharide (Ft LPS), wherein said antibody lacks an Fc region or has an impaired Fc-region. As a result of the missing or impaired Fc region said antibody cannot bind FcγR.

The term "*Francisella tularensis* (also referred to herein as "*F. tularensis*" or "Ft") LPS" refers to the lipopolysaccharide (LPS, endotoxin) of *Francisella tularensis*. Ft is the Gram negative bacterium that causes tularemia.

LPS is the primary constituent of the outer leaflet of the outer membrane of Gram-negative bacteria. The structure of LPS includes a lipid portion (lipid A) that anchors it into the membrane, a polysaccharide core and an oligo- or polysaccharide (also termed OAg) extending from the core beyond the bacterial surface. *Francisella* LPS is structurally different from most commonly studied LPS of other gram negative bacteria (Gunn et al. 2007; Okan & Kasper 2013).

As indicated above, the present invention provides isolated monoclonal antibodies that bind to Ft LPS. The term "antibody" refers to a polypeptide encoded by an immunoglobulin gene that specifically binds and recognizes an antigen, in the present case Ft LPS.

The term "monoclonal antibody", "monoclonal antibodies" or "mAb" as herein defined refers to a population of substantially homogenous antibodies, i.e., the individual antibodies comprising the population are identical except for possibly naturally occurring mutations that may be present in minor amounts. Monoclonal antibodies are directed against a single antigenic site (epitope).

Monoclonal antibodies may be prepared and purified by any method known in the art. For example, monoclonal antibodies may be prepared from B cells taken from the spleen or lymph nodes of immunized animals (e.g. rabbits, rats, mice or monkeys), by fusion with immortalized B cells under conditions which favor the growth of hybrid cells.

Immunization of animals may be carried out by any method known in the art, for example by immunizing rabbits with live LVS, as described below. The immunized rabbits are then sacrificed and samples are taken from their blood and lymphatic nodes in order to isolate mRNA that will be used for variable heavy and variable light (VH/VL) chain amplification and further used for example for constructing a phage display library, in order to select active antibodies. Based on the results obtained from a phage display library, full length antibodies are produced, as known in the art and as described below.

Purification of monoclonal antibodies may be performed using any method known in the art, for example by affinity chromatography, namely, by using an affinity column to which a specific epitope (or antigen) is conjugated. Alternatively purification of antibodies may be based on using protein A and protein G column chromatography, as described below.

An exemplary antibody structural unit comprises a tetramer, as known in the art. Each tetramer is composed of two identical pairs of polypeptide chains, each pair having one "light chain" and one "heavy chain". The N-terminus of each chain defines a variable region of about 100 to 110 or more amino acids primarily responsible for antigen (or epitope) recognition.

Thus, the terms "heavy chain variable region" ($V_H$) and "light chain variable region" ($V_L$) refer to these heavy and light chains, respectively. More specifically, the variable region is subdivided into hypervariable and framework (FR) regions. Hypervariable regions have a high ratio of different amino acids in a given position, relative to the most common amino acid in that position. Four FR regions which have more stable amino acids sequences separate the hypervariable regions. The hypervariable regions directly contact a portion of the antigen's surface. For this reason, hypervariable regions are herein referred to as "complementarity determining regions", or "CDRs", the CDRs are positioned either at the heavy chain of the antibody (a "heavy chain complementarity determining region") or at the light chain of the antibody (a "light chain complementarity determining region").

From N-terminal to C-terminal, both light and heavy chains comprise the domains FR1, CDR1, FR2, CDR2, FR3, CDR3 and FR4. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, the complementarity determining regions CDRH1, CDRH2 and CDRH3 refer to the three complementarity determining regions starting from the N-terminus of the antibody's heavy chain (also referred to herein as heavy chain complementarity determining region) and the complementarity determining regions CDRL1, CDRL2 and CDRL3 refer to the three complementarity determining regions starting from the N-terminus of the antibody's light chain (also referred to herein as light chain complementarity determining region).

The present invention encompasses antigen-binding fragments of the isolated anti Ft LPS monoclonal antibody of the invention.

As used herein the term "antigen binding fragment" relates to a fragment of the full length antibody which retains the antibody's specificity of binding to Ft LPS. An antigen binding fragment encompasses but is not limited to Fv, single chain Fv (scFv), heavy chain variable region capable of binding the antigen, light chain variable region capable of binding the antigen, Fab', Fab, F(ab')$_2$ and F(ab)$_2$.

Such fragments may be produced by any method known in the art, for example by proteolytic cleavage, using enzymes such as papain (to produce Fab fragments) or pepsin (to produce F(ab')$_2$ fragments).

Thus in some embodiments the antibody according to the invention is wherein said antibody is an antibody fragment selected from the group consisting of Fv, single chain Fv (scFv), heavy chain variable region capable of binding the antigen, light chain variable region capable of binding the antigen, Fab', Fab, F(ab')$_2$, F(ab)$_2$ and any combination thereof. In some embodiments, the antibody or antigen-binding fragment thereof is a single chain variable fragment (scFv) molecule.

In some specific embodiments, the antibody is a mutated IgG that lacks the ability to bind to IgG receptors.

In some embodiments, the antibody of the invention lacks an Fc region or has an impaired Fc-region. By the term "impaired" as used herein it is meant to include any damage, defect or imperfection in the Fc-region that renders the antibody less proficient in binding the FcR, e.g. FcγR.

In embodiments wherein the antibody lacks an Fc region or has an impaired Fc region it cannot bind the FcγR.

As used herein the term "FcR" or "Fc Receptor" refers to a protein receptor found on the surface of various cells of the immune system, which has a binding specificity for the Fc (Fragment, crystallizable) region of an antibody. In particular, the "FcγR" or "FcγReceptor" which binds IgG.

The term "cannot bind the FcγR" refers to a reduction of at least about 10%, 20%, 30%, 40%, 50%, 60%, 70%, 80%, 90%, 100% in the binding of the antibody of the invention to FcγR as compared to a corresponding antibody comprising an undamaged Fc domain. Determination of binding of an antibody to the FcγR may be performed by methods well known in the art. In specific embodiments the present disclosure provides an isolated monoclonal antibody or antigen-binding fragment thereof which binds to *F. tularensis* lipopolysaccharide (Ft LPS), wherein said antibody lacks an Fc region or has an impaired Fc-region, wherein the isolated monoclonal antibody or antigen-binding fragment thereof cannot bind Fc-gamma receptor (FcγR).

As detailed above, lipopolysaccharide (LPS) is the primary constituent of the outer leaflet of the outer membrane of Gram-negative bacteria. The structure of LPS includes a lipid portion, a polysaccharide core and an oligo- or polysaccharide (also termed Oag or O-antigen). The O-antigen is a repetitive glycan polymer and the composition thereof varies from strain to strain.

In specific embodiments the isolated monoclonal antibody of the invention or the antigen-binding fragment thereof binds to the O-polysaccharide (O-antigen) chain of Ft LPS. In further specific embodiments the isolated monoclonal antibody of the invention or the antigen-binding fragment thereof binds to the four-sugar repeats in the Ft LPS OAg chains.

In various embodiments binding of the isolated monoclonal antibody of the invention or the antigen-binding fragment thereof to Ft LPS is characterized by a dissociation constant (Kd) smaller than $1 \times 10^{-7}$ l/s.

As demonstrated in Example 4 below, binding of TL1-scFv inhibited *F. tularensis* uptake by macrophages. Therefore in particular embodiments the isolated monoclonal antibody of the invention or the antigen-binding fragment thereof inhibits Ft uptake by cells in a subject.

By the term "inhibit" in the context of the present invention it is meant that the isolated monoclonal antibody of the invention or the antigen-binding fragment thereof impedes, hinders, prohibits or suppresses by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% *F. tularensis* uptake by macrophages as compared to *F. tularensis* uptake by macrophages in the absence of the antibody of the invention or the antigen-binding fragment thereof.

The term "cell" or "cells" as referred to herein is used at its broadest sense.

In some embodiments the isolated anti *F. tularensis* LPS monoclonal antibody is a chimeric antibody, a human antibody or a humanized antibody.

The term "chimeric" antibodies as herein defined refers to antibodies in which a portion of the heavy and/or light chain is derived from a particular species, while the remainder of the chain(s) is derived from another species, e.g. mouse, rat, rabbit or non-human primate.

Methods for preparing chimeric antibodies are well known in the art.

The term "humanized" antibodies traditionally refers antibodies that contain a human-derived immunoglobulin framework with minimal sequences derived from non-human immunoglobulin at the CDRs and optionally at additional relevant positions. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and activity.

The term "human antibody" as used herein refers to an antibody that possesses an amino acid sequence corresponding to that of an antibody produced by a human and/or has been made using any of the techniques for making human antibodies known in the art. This definition specifically excludes a humanized antibody that comprises non-human antigen-binding residues.

Preparation of humanized and human antibodies is well known in the art. Antibodies may also be prepared using phage display. As known in the art, antibody phage display (APD) is based on genetic engineering of bacteriophages and repeated rounds of antigen-guided selection and phage propagation.

The APD process begins with antibody-library preparation (e.g. as described in the Examples section below), by preparation of quality RNA from the cell source chosen (e.g., lymph nodes and blood samples). This RNA is reverse-transcribed into cDNA, which is used for PCR of the VH and VL chains of the encoded antibodies. This step is followed by ligation of the variable heavy (VH) and variable light (VL) PCR products into a phage display vector, culminating in analysis of clones of mAbs.

For preparing large quantities of the antibody (either chimeric, humanized or human), a stable cell line expressing the antibody can be prepared, by transfecting cells (e.g. CHO cells) with the Ig expression vector containing both heavy and light chains of the antibody. The antibodies may then be manufactured in a state of the art single-use bioreactor system. The antibodies may be purified to clinical grade using well established monoclonal antibody purification methods. Highly anti-Ft LPS antibody producing clones may be then selected and expanded based on antibody levels in the supernatant, as tested by any method known in the art, for example, an Ft LPS-specific ELISA assay, as detailed herein below. A master cell bank, developed for the specific clone, may serve as the starting growing material for all clinical grade batches.

In some embodiments, the present invention provides an anti Ft LPS isolated monoclonal antibody or antigen-binding fragment thereof, wherein said antibody lacks an Fc region or has an impaired Fc-region and wherein said antibody or antigen-binding fragment thereof comprises a heavy chain complementarity determining region (CDRH) 1 denoted by SEQ ID NO. 5, a CDRH2 denoted by SEQ ID NO. 6, a CDRH3 denoted by SEQ ID NO. 7, and a light chain complementarity determining region (CDRL) 1 denoted by SEQ ID NO. 8, a CDRL2 denoted by SEQ ID NO. 9, and a CDRL3 denoted by SEQ ID NO. 10.

In some embodiments, the present invention provides an anti Ft LPS isolated monoclonal antibody or antigen-binding fragment thereof, wherein said antibody lacks an Fc region or has an impaired Fc-region and wherein said antibody or antigen-binding fragment thereof comprises a heavy chain variable region and a light chain variable region, wherein said heavy chain variable region is encoded by a nucleic acid sequence which is at least 70%, or 75%, or 80%, or 85%, or 90% or more identical to the nucleic acid sequence denoted by SEQ ID NO. 1 and wherein said light chain variable region is encoded by a nucleic acid sequence which is at least 70%, or 75%, or 80%, or 85%, or 90% or more identical to the nucleic acid sequence denoted by SEQ ID NO. 2.

In particular embodiments the isolated monoclonal antibody or antigen-binding fragment thereof comprises a heavy chain variable region and a light chain variable region, the heavy chain variable region is encoded by a nucleic acid sequence which is at least 70%, or 75%, or 80%, or 85%, or 90% or more identical to the nucleic acid sequence denoted by SEQ ID NO. 1 and the light chain variable region is encoded by a nucleic acid sequence which is at least 70%, or 75%, or 80%, or 85%, or 90% or more identical to SEQ ID NO. 2 and the isolated monoclonal antibody or antigen-binding fragment thereof maintains the biological activity of the antibody of the invention as herein defined, for example of an antibody comprising a heavy chain variable region and a light chain variable region, the heavy chain variable region encoded by a nucleic acid sequence denoted by SEQ ID NO. 1 and the light chain variable region is encoded by a nucleic acid sequence denoted by SEQ ID NO. 2.

In some embodiments, the present invention provides an anti Ft LPS isolated monoclonal antibody or antigen-binding fragment thereof, wherein said antibody lacks an Fc region or has an impaired Fc-region, and wherein said antibody or antigen-binding fragment thereof comprises a heavy chain variable region comprising the amino acid sequence denoted by SEQ ID NO. 3 or a variant thereof and a light chain variable region comprising the amino acid sequence denoted by SEQ ID NO. 4, or a variant thereof.

In other embodiments the isolated antibody according to the invention is wherein said antibody is an anti Ft LPS isolated monoclonal antibody or antigen-binding fragment thereof, wherein said antibody lacks an Fc region or has an impaired Fc-region, and wherein said antibody comprises six CDR sequences as denoted by SEQ ID Nos 5-10, and a heavy chain variable region having at least 90% sequence homology to SEQ ID NO:3 and a light chain variable region having at least 90% sequence homology to SEQ ID NO: 4.

In one specific embodiment the isolated antibody according to the invention is an scFv antibody comprising six CDR sequences as denoted by SEQ ID Nos 5-10, and a heavy chain variable region having at least 90% sequence homology to SEQ ID NO:3 and a light chain variable region having at least 90% sequence homology to SEQ ID NO: 4.

In another embodiment, the present invention provides an isolated monoclonal antibody that binds the same epitope as an antibody comprising:

(a) a heavy chain CDR1 comprising SEQ ID NO: 5, a heavy chain CDR2 comprising SEQ ID NO: 6, and a heavy chain CDR3 comprising SEQ ID NO: 7; and (b) a light chain CDR1 comprising SEQ ID NO: 8, a light chain CDR2 comprising SEQ ID NO: 9, and a light chain CDR3 comprising SEQ ID NO: 10.

The nucleic acid sequence and the amino acid sequence, as well as the sequences of the CDRs are displayed in Table 1.

TABLE 1

| SEQ ID NO. | Sequence | Description |
|---|---|---|
| 1 | CAGTCGTTGGAGGAGTCCGGGGGAGACCTGGTCAAACCTGGG GCATCCCTGACACTCACCTGCACAGCCTCTGGATTCACCCTC AGTAGCTACTGGATTTCCTGGGTCCGCCAGGCTCCAGGGAAG GGGCTGGAGTGGATCGCATCGTTTAGTACTTTTTATGAAAAT GGAAATTACGCGGACTGGGCGAAAGGCCGATTCACCGTCTCC AAATCCTCGTCGACCACGGTGACTCTGCAAATGACCAGTCTG ACAGCCGCGGACACGGCCACCTATTTCTGTGGGAGAGGGGAG TATATTAATGATAATGATTTTCCATACAGGTTGTGGGGCCCA GGCACCCTGGTCACCGTCTCTTCA | Heavy chain nucleic acid sequence |
| 2 | GATGTCGTTATGACCCAGACTCCAGCCTCCGTGTCTGCAGCT GTGGGAGGCACAGTCACCATCAAGTGCCAGGCCAGTGAGAGC ATTAATAGTAGATTAGCCTGGTATCAGCAGAAACGAGGGCAG CGTCCCAAGCTCCTGATCTATTCTGCATCCACTCTGGAATCT GGGGTCCCATCGCGGTTCAAGGGCAGTGGATCTGGGACAGAG TACACTCTCACCATCAGCGACCTGGAGTGTGCCGATGCTGCC ACTTACTACTGTCAAACCTATTATGATAGTGGTAGTAGTGCT AATGATTTCGGCGGAGGGACCGAGGTGGTCGICGAA | Light chain nucleic acid sequence |
| 3 | QSLEESGGDLVKPGASLTLTCTASGFTLSSYWISWVRQAPGK GLEWIASFSTFYENGNYADWAKGRFTVSKSSSTTVTLQMTSL TAADTATYFCGRGEYINDNDFPYRLWGPGTLVTVSS | Heavy chain amino acid sequence |
| 4 | DVVMTQTPASVSAAVGGTVTIKCQASESINSRLAWYQQKRGQ RPKLLIYSASTLESGVPSRFKGSGSGTEYTLTISDLECADAA TYYCQTYYDSGSSANDFGGGTEVVVE | Light chain amino acid sequence |
| 5 | SYWIS | Heavy chain CDR H1 |
| 6 | SFSTFYENGNYADWAKG | Heavy chain CDR H2 |
| 7 | GEYINDNDFPYRL | Heavy chain CDR H3 |
| 8 | QASESINSRLA | Light chain CDR H1 |

TABLE 1 -continued

| SEQ ID NO. | Sequence | Description |
|---|---|---|
| 9 | SASTLES | Light chain CDR H2 |
| 10 | QTYYDSGSSAND | Light chain CDR H3 |

The CDR sequences are shown in bold within the heavy and the light chain amino acid sequences.

The present invention also encompasses variants of the heavy and light chain variable regions. The variants may include mutations in the complementarity determining regions of the heavy and light chains which do not alter the activity of the antibodies herein described, or in the framework region.

By the term "variant" it is meant sequences of amino acids or nucleotides different from the sequences specifically identified herein, in which one or more amino acid residues or nucleotides are deleted, substituted or added.

It should be appreciated that by the term "added", as used herein it is meant any addition of amino acid residues to the sequences described herein.

Variants encompass various amino acid substitutions. An amino acid "substitution" is the result of replacing one amino acid with another amino acid which has similar or different structural and/or chemical properties. Amino acid substitutions may be made on the basis of similarity in polarity, charge, solubility, hydrophobicity, hydrophilicity, and/or the amphipathic nature of the residues involved.

Typically, variants encompass conservative amino acid substitutions. Conservative substitution tables providing functionally similar amino acids are well known in the art. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Each of the following eight groups contains other exemplary amino acids that are conservative substitutions for one another.
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

Variants in accordance with the invention also encompass non-polar to polar amino acid substitutions and vice-versa.

As used herein, the term "amino acid" or "amino acid residue" refers to naturally occurring and synthetic amino acids, as well as amino acid analogs and amino acid mimetics that function in a manner similar to the naturally occurring amino acids.

Variant sequences refer to amino acid or nucleic acids sequences that may be characterized by the percentage of the identity of their amino acid or nucleotide sequences with the amino acid or nucleotide sequences described herein (for example, the amino acid or nucleotide sequences of the heavy and light chains of the antibodies herein described).

In some embodiments, variant sequences as herein defined refer to nucleic acid sequences that encode the heavy and light chain variable regions, each having a sequence of nucleotides with at least 70% or 75% of sequence identity, around 80% or 85% of sequence identity, around 90%, 91%, 92%, 93%, 94%, 95%, 96%, 97%, 98% or 99% of sequence identity when compared to the sequences of the heavy and light chain variable regions described herein.

By the term "activity of the antibodies" it is meant the ability of the antibodies to bind Ft LPS, and preferably to reduce bacterial uptake by a subject's cells. The activity of the antibodies can be measured in vivo or in vitro using methods well known in the art, e.g. as described in the Examples below.

The binding of the antibody of the invention to its target protein may be measured for example using ELISA, biolayer interferometry (BLI), Western blot or IFA assays.

The biological activity of the antibodies can be measured for example in a functional assay testing reduction of bacterial uptake by cultured macrophages.

In another one of its aspects the present invention provides an isolated nucleic acid molecule comprising a nucleotide sequence encoding an antibody or antigen-binding fragment thereof according to the invention.

The term "nucleic acid" or "nucleic acid molecule" as herein defined refers to a polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase).

The invention further provides an expression vector comprising the isolated nucleic acid molecule as herein defined.

"Expression vector" sometimes referred to as "expression vehicle" or "expression construct", as used herein, encompasses vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. The expression vector in accordance with the invention may be competent with expression in bacterial, yeast, or mammalian host cells, to name but few.

In yet another one of its aspects the present invention provides a host cell transfected with the isolated nucleic acid molecule according to the invention or with the expression vector according to the invention.

The term "host cells" as used herein refers to cells which are susceptible to the introduction of the isolated nucleic acid molecule according to the invention or with the expression vector according to the invention. Preferably, said cells are mammalian cells, for example CHO cells or NS0 cells. Transfection of the isolated nucleic acid molecule or the expression vector according to the invention to the host cell may be performed by any method known in the art.

In yet another one of its aspects the present invention provides an immunoconjugate comprising the antibody or antigen-binding fragment thereof according to the invention and an additional therapeutic agent as defined herein below.

The term "immunoconjugate" as herein defined refers to an antibody or antigen-binding fragment thereof according to the invention that is conjugated (linked or joined) to an additional agent. Immunoconjugates may be prepared by any method known to a person skilled in the art, for example, by cross-linking the additional agent to the antibody according to the invention or by recombinant DNA methods.

The anti Ft LPS antibody of the invention may be administered in combination with at least one additional therapeutic agent.

The term "additional therapeutic agent" used herein refers to any agent that may be used for treating Ft infection. In accordance with certain embodiments said at least one additional therapeutic agent is selected from a group consisting of anti Ft antibodies, antibiotics, or agents capable of modulating the immune response against the Ft infection.

In certain embodiments the additional therapeutic agent is an additional antibody. The term "additional antibody" as herein defined refers to an antibody, which is not the antibody according to the invention, which may be used in combination with the antibody of the invention.

The present invention further provides a pharmaceutical composition comprising as an active ingredient the isolated anti Ft LPS antibody of the invention, or antigen-binding fragment thereof or the immunoconjugate as herein defined and a pharmaceutically acceptable carrier, excipient or diluent.

In a specific embodiment, said pharmaceutical composition is for use in the treatment of an Ft infection (i.e. tularemia) or for use in inhibiting Ft uptake by the subject's cells.

The "pharmaceutical composition" of the invention generally comprises the antibody or any antigen-binding fragment thereof as herein defined and a buffering agent, an agent which adjusts the osmolarity of the composition and optionally, one or more pharmaceutically acceptable carriers, excipients and/or diluents as known in the art.

As used herein the term "pharmaceutically acceptable carrier, excipient or diluent" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

In other embodiments the pharmaceutical composition according to the invention further comprises an additional therapeutic agent. Non-limiting examples of additional therapeutic agents include anti Ft antibodies, antibiotics (e.g. aminoglycosides, tetracyclines, or fluoroquinolones), or agents capable of modulating the immune response against the Ft infection. Thus in specific embodiments the pharmaceutical composition according to the invention further comprises an additional therapeutic agent which is an antibiotic.

In specific embodiments the present invention relates to a pharmaceutical composition comprising an isolated anti Ft LPS antibody, or any antigen-binding fragment thereof, wherein the antibody comprises a heavy chain variable region of the amino acid sequence denoted by SEQ ID NO. 3 or a variant thereof and a light chain variable region of the amino acid sequence denoted by SEQ ID NO. 4, or a variant thereof.

The present invention also provides methods of prophylaxis, treatment or amelioration of Ft infection or tularemia comprising administering to a subject in need thereof a therapeutically effective amount of the isolated monoclonal antibody or antigen-binding fragment thereof of the invention, or an immune-conjugate comprising the antibody or antigen-binding fragment thereof of the invention or a pharmaceutical composition comprising the isolated monoclonal antibody or antigen-binding fragment thereof or the immune-conjugate of the invention.

The term "Ft infection" is used herein at its broadest sense and refers to any infection caused by *Francisella tularensis* (Ft). The term "tularemia" as known in the art refers to an infectious disease caused by the bacterium Ft. Symptoms include for example fever, skin ulcer, enlarged lymph nodes, pneumonia or a throat infection.

The invention also provides a method of inhibiting Ft uptake by cells in a subject comprising administering to a subject in need thereof a therapeutically effective amount of the isolated monoclonal antibody or antigen-binding fragment thereof of the invention, or an immune-conjugate comprising the antibody or antigen-binding fragment thereof of the invention or a pharmaceutical composition comprising the isolated monoclonal antibody or antigen-binding fragment thereof or the immune-conjugate of the invention.

The terms "subject" or "patient" are used interchangeably and refer to a subject that may benefit from the present invention such as a mammal (e.g. canine, feline, ovine, porcine, equine, bovine, or human). In one specific embodiment the patient is human. Diagnosis of Ft infection may be performed by a skilled physician by methods known in the art. The term "subject in need thereof" in the context of the present invention inter alia refers to mammals and in particular to human subjects suffering from Ft infection or tularemia as defined herein.

By the term "prophylaxis" as herein defined it is meant to provide a "preventive treatment" or "prophylactic treatment", namely acting in a protective manner, to defend against or prevent the appearance of a symptom of an Ft infection, or tularemia onset or progression.

It is to be understood that the terms "treat", "treating", "treatment" or forms thereof, as used herein, mean reducing, preventing, curing, reversing, ameliorating, attenuating, alleviating, minimizing, suppressing or halting the deleterious effects of a disease or a condition or delaying the onset of one or more clinical indications of an Ft infection, or tularemia, as defined herein. In some embodiments the methods according to the invention are wherein said methods further comprise administering to a subject in need thereof an additional therapeutic agent as herein defined.

Administration according to the present invention may be performed by any of the following routes: oral administration, intravenous, intramuscular, intraperitoneal, intrathecal or subcutaneous injection; intra-rectal administration; intranasal administration, ocular administration or topical administration.

In specific embodiments administration according to the present invention may be performed intravenously. In other specific embodiments administration may be performed intraperitoneally. In other specific embodiments administration may be performed by inhalation.

The antibodies or antibody fragments as herein defined, any pharmaceutical compositions comprising the same or any conjugates comprising them may be administered to a subject prior to or post disease onset, in a single dose or in multiple doses.

Thus in some embodiments the method of prophylaxis, treatment or amelioration of Ft infection according to the invention is where said isolated anti Ft LPS antibody or any antigen-binding fragment thereof according to the invention, or pharmaceutical composition according to the invention is administered to said subject prior to or after disease onset.

A "therapeutically effective amount" of the isolated monoclonal antibody or any antigen-binding fragment thereof according to the invention, or the pharmaceutical composition according to the invention for purposes herein defined is determined by such considerations as are known in the art in order to cure, arrest or at least alleviate or ameliorate the medical condition. For any preparation used in the methods of the invention, the dosage or the therapeutically effective amount can be estimated initially from in vitro cell culture assays or based on suitable animal models.

In some embodiments the therapeutically effective amount in accordance with the invention is in the range of 10 µg/kg to about 50 mg/kg.

In other embodiments the therapeutically effective amount in accordance with the invention is in the range of 0.1 mg/kg to 40 mg/kg, 1 mg/kg to 10 mg/kg, or 5 mg/kg to 10 mg/kg.

In other embodiments the isolated anti Ft LPS antibody or any antigen-binding fragment thereof according to the invention or pharmaceutical composition according to the invention is administered to the subject as a single dose or as multiple doses.

Specific exemplary doses include, but are not limited to 0.75 mg/kg, or 2.5 mg/kg, or 5 mg/kg, or 10 mg/kg each given as a single daily dose. In one embodiment, the doses are given intravenously.

The present invention further provides the isolated anti Ft LPS antibody or any antigen-binding fragment thereof according to the invention or the pharmaceutical composition according to the invention for use in a method of prophylaxis, treatment or amelioration of an Ft infection or tularemia as defined herein.

Still further the present invention provides use of the isolated monoclonal antibody or antigen-binding fragment thereof, the immune-conjugate comprising the antibody or antigen-binding fragment thereof or the pharmaceutical composition comprising the isolated monoclonal antibody or antigen-binding fragment thereof or the immune-conjugate of the invention in the preparation of a medicament for the prophylaxis, treatment or amelioration of Ft infection or tularemia or in the preparation of a medicament for inhibiting Ft uptake by cells in a subject.

In specific embodiments the invention provides an isolated scFv anti Ft LPS antibody fragment, wherein the antibody fragment comprises a heavy chain variable region of the amino acid sequence denoted by SEQ ID NO. 3 or a variant thereof and a light chain variable region of the amino acid sequence denoted by SEQ ID NO. 4, or a variant thereof for use in a method of prophylaxis, treatment or amelioration of Ft infection or tularemia as defined herein.

It is appreciated that the term "purified" or "isolated" refers to molecules, such as amino acid or nucleic acid sequences, peptides, polypeptides or antibodies that are removed from their natural environment, isolated or separated. An "isolated antibody" is therefore a purified antibody. As used herein, the term "purified" or "topurify" also refers to the removal of contaminants from a sample.

In another aspect, the present invention provides an isolated monoclonal antibody or antigen-binding fragment thereof which binds to *F. tularensis* LPS, wherein said antibody comprises a heavy chain complementarity determining region (CDRH) 1 denoted by SEQ ID NO. 5, a CDRH2 denoted by SEQ ID NO. 6, a CDRH3 denoted by SEQ ID NO. 7, and a light chain complementarity determining region (CDRL) 1 denoted by SEQ ID NO. 8, a CDRL2 denoted by SEQ ID NO. 9, and a CDRL3 denoted by SEQ ID NO. 10.

The antibody is also termed herein TL1.

In certain embodiments, the isolated monoclonal antibody comprises a heavy chain variable region and a light chain variable region, wherein said heavy chain variable region is encoded by a nucleic acid sequence which is at least 70% identical to the nucleic acid sequence denoted by SEQ ID NO. 1 and wherein said light chain variable region is encoded by a nucleic acid sequence which is at least 70% identical to SEQ ID NO. 2.

In certain embodiments, the isolated monoclonal antibody comprises a heavy chain variable region comprising the amino acid sequence denoted by SEQ ID NO. 3 or a variant thereof and a light chain variable region comprising the amino acid sequence denoted by SEQ ID NO. 4, or a variant thereof.

The invention also provides an isolated nucleic acid molecule comprising a nucleotide sequence encoding the above antibody, as well as an expression vector comprising the isolated nucleic acid molecule and a host cell transfected with the expression vector.

As shown in the Examples below, the TL1 antibody of the invention exhibits ultra-high affinity of binding to Ft LPS.

In light of the very high affinity and specificity of the TL1 antibody towards Ft, and in light of its very high sensitivity in detecting the virulent SchuS4 strain as shown in the Examples below, the antibody of the invention can be used for sensitive detection of Ft bacteria.

Accordingly, in another aspect, the present invention provides a method of detecting Ft LPS in a biological sample obtained from a subject, said method comprising:
  a. contacting said biological sample with the isolated monoclonal antibody or antigen-binding fragment thereof of the invention; and
  b. detecting said isolated monoclonal antibody or any antigen-binding fragment thereof;
wherein the presence of said isolated monoclonal antibody or any antigen-binding fragment thereof indicates the presence of Ft in said biological sample.

Detecting the isolated antibodies in accordance with the present invention may be performed by any method known in the art, for example by immobilizing the antibody of the invention as the capture reagent in an ELISA assay. In various embodiments the isolated antibodies in accordance with the present invention may be labeled according to any methods known in the art. In other embodiments detection may be based on identifying said antibodies using secondary antibodies. Other detection assays include, but are not limited to Biolayer interferometry-based assay (Mechaly et al. 2016).

The term "biological sample" is used herein in its broadest sense and refers to any sample taken from a subject as herein defined in which Ft LPS may be detected. Biological samples may be obtained from mammals (including humans) and encompass fluids, solids and tissues. In some embodiments the biological sample is blood, plasma, serum, lymph fluid, urine, a tissue sample, a biopsy sample or a cell lysate. In another aspect, the present invention provides a method of treating Ft infection by administering to a subject in need thereof a therapeutically effective amount of the scFv molecule of the invention.

In another aspect, the present invention provides a method of inhibiting Ft uptake by macrophages, the method comprising administering to a subject in need thereof a therapeutically effective amount of the scFv molecule of the invention.

The method may further comprise administration of an additional therapeutic agent, e.g. an antibiotic.

The present disclosure further provides a kit for detecting Ft infection comprising:

(a) at least one isolated monoclonal antibody or antigen-binding fragment thereof according to the present disclosure;

(b) means for detection of said isolated monoclonal antibody; and optionally (c) instructions for use of said kit.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Examples

Materials and Methods

Bacterial and Cell Cultures

*Francisella tularensis* subsp. *tularensis* (Schu S4) strain and *Francisella tularensis* subsp. *holarctica* strain LVS were grown as described before (Bar-On et al. 2017). The bioluminescence reporter plasmid pXB173-lux was obtained from James E. Bina (Bina et al. 2010) and introduced into wild-type *F. tularensis* LVS, resulting in constitutive bioluminescence production. In order to increase the bioluminescent signal, the original gro promoter was replaced with the bfr promoter, which has been found to be more potent (Zaide et al. 2011). The resulting LVS-pXB173-lux was grown in TSBC broth (0.1% L-cysteine, 3% tryptic soy broth) or CHA agar (1% hemoglobin, 5.1% Cysteine heart agar) supplemented with 2 µg/ml chloramphenicol (Cm).

J774A.1 murine macrophage like cells were obtained from the American Type Culture Collection (ATCC, BALB/C macrophage). The cells were grown in flasks in Dulbecco's Modified Eagle Medium (DMEM, Biological Industries, Beit Haemek, Israel) supplemented with 10% fetal bovine serum (FBS), 2 mM L-glutamine and 1 mM sodium pyruvate and maintained at 370 C in a humidified 5% CO2 incubator.

LPS was purified from LVS bacteria as described before (Phillips et al. 2004). LVS and LVS-S were inactivated by exposure of $5 \times 10^9$ CFU/ml to 3 doses of 75,000 µj/cm3 UV radiation. SchuS4 was inactivated by boiling approximately $8.5 \times 10^{10}$ CFU/ml in 2×Laemmli sample buffer (Bio-Rad, USA) for 30 min.

Rabbit Immunization

Treatment of animals was in accordance with regulations outlined in the U.S. Department of Agriculture (USDA) Animal Welfare Act and the conditions specified in the Guide for Care and Use of Laboratory Animals (National Institute of Health, 2011). The rabbit immunization study was approved by the local ethical committee on animal experiments. Live LVS strain was used to immunize a female New Zealand White (NZW) *Oryctolagus cuniculus* (rabbit). The rabbit was injected with 6 consecutive subcutanic injections over a period of 24 weeks. The first four injections consisted of 1 ml of $1 \times 10^8$ CFU that were given monthly, with the exception of the $4^{th}$ injection that was given two months after the $3^{rd}$ injection. The next two monthly booster injections consisted of $1 \times 10^9$ CFU. Seven days after the last boost, the rabbit was sacrificed and samples were taken from its blood and lymphatic nodes for library construction, as described in Mechaly et al. 2018.

Antibodies

Anti *F. tularensis* polyclonal IgG fraction (designated T5) was obtained by HiTrap Protein A chromatography (GE Healthcare, Uppsala, Sweden) of the hyper-immune rabbit serum immunized as described in the previous section. The chromatography was carried out according to the manufacturer's instructions and the resulting IgG fraction was dialyzed against PBS pH 7.4.

scFv Library Construction

RNA was extracted from lymph nodes and blood samples and was used as a template for first-strand cDNA synthesis, essentially as described in Mechaly 2018. A set of degenerate primers was designed based on published data and was used to amplify all known sequences of *Oryctolagus cuniculus* VH and Vk immunoglobulin families (Mechaly et al. 2018). The construction of the scFv library was performed by assembly PCR of the VH and Vκ fragments (Noy-Porat et al. 2016). The scFv gene fragments were then ligated into linearized pCC$_{16}$ plasmid (Rosenfeld et al. 2009) and transformed into *E. coli* MC1061F electro-competent cells (Lucigen, Middleton, Wis., USA). The transformed bacteria, containing the final scFv library, were plated on YPD agar (BD, Franklin Lakes, N.J., USA) supplemented with 100 µg/mL ampicillin and 100 mM glucose and, after an overnight culture at 30° C., were harvested, aliquoted and stored at −80° C.

Library Screening

For library packaging, 200 mL YPD medium, containing 100 µg/mL ampicillin and 100 mM glucose, were inoculated with 0.5 mL of the scFv library. Bacteria were grown in a shaker incubator (New Brunswick Scientific, Enfield, Conn., USA) at 37° C., 220 rpm to an O.D.$_{600}$ of 0.7-0.9. Twenty-five milliliters of bacteria were than infected with 125 µL of M13KO7 helper phage (New England Biolabs, Ipswich, Mass., USA) by incubating at 37° C. for 30 min without shaking, followed by 30 min at 120 rpm. Infected cells were harvested (5 min, 4000 rpm) and re-suspended in 100 mL YPD with 100 µg/mL ampicillin and 50 µg/mL kanamycin. After an overnight culture at 30° C. at 200 rpm, cells were pelleted by centrifugation for 10 min, 4000 rpm at 4° C., and the supernatant containing the phages was filtered through a 0.45-µm filter and then precipitated with ⅕ volume of 20% PEG6000 (polyethylene glycol)/2.5 M NaCl solution for 2 h on ice. The phages were pelleted by centrifugation for 1 h at 9000×g, 4° C., and re-suspended in 5 mL PBS.

For library panning, inactivated LVS were used (1×10$^8$ cfu/mL in Carbonate bicarbonate) to coat a polystyrene immuno-tube (Nunc, Denmark). The bacterial solution was then removed, and the tube was blocked (2% SM+0.05% Tween 20 in PBS). Approximately 1×10$^{12}$ phage clones were blocked for 1 h and then incubated for an additional hour with the LVS coated immuno-tube. The immune-tube was then washed twice with blocking solution, 4 times with PBST (PBS, 0.05% Tween 20) and twice with PBS. Bound phage were eluted with 1 mL 100 mM trimethylamine pH 3 (Sigma-Aldrich, St. Louis, Mo., USA) for 30 min and the neutralized eluate (in 200 µL 1M tris pH 7.4) was used to infect 5 mL of *E. coli* TGI strain (Lucigen, Middleton, Wis., USA). Infection was carried out at 37° C. for 30 min without shaking followed by 30 min at 120 rpm. 3 mL of *E. coli* TG were directly used to infect the immuno-tube, in order to amplify strong binders that were not eluted with the low pH elution buffer. The bacteria were plated on YPD agar plates with 100 µg/mL ampicillin and 100 mM glucose, cultured overnight at 30° C., and clones were then harvested into 30 mL YPD-100 µg/mL ampicillin-100 mM glucose-20% glycerol solution. 100 µL of the harvested clones were used for phage packaging in 25 mL medium, as described above. Two additional panning rounds were conducted as described, except that 10$^{11}$ and 10$^{10}$ phage clones were used as input, respectively. The blocker was alternated (with 3% BSA+0.05% Tween20 for the 2$^{nd}$ panning step and 2% SM+0.05% Tween 20 for the 3$^{rd}$) and the stringency of the washing steps was elevated to include 5 washes with blocking solution, 10 washes with PBST and 2 with PBS for the 2$^{nd}$ panning step and 10 washes with blocking solution, 15 washes with PBST and 2 with PBS for the 3$^{rd}$ panning step. Single colonies were randomly picked from the third panning output, and phages were rescued and tested for their binding to LVS bacteria.

ELISA

Direct ELISA: Maxisorp 96-well microtiter plates (Nunc, Sigma-Aldrich, St. Louis, Mo., USA) were coated overnight (50 µL/well) with 2×10$^8$ CFU/mL of inactivated LVS in Carbonate bicarbonate buffer (Sigma-Aldrich, St Louis, Mo., USA), then washed and blocked with PBST buffer (0.05% Tween 20, 2% BSA in PBS) for one hour. Individual phage clones, antibodies or rabbit sera were added to the plates for a one-hour incubation; the plates were then washed with PBST and incubated with the detecting antibody: horseradish peroxidase (HRP)-conjugated anti-M13 antibody (GE healthcare, Little Chalfont, UK) for phage clones, anti-human IgG conjugated to alkaline phosphatase (Jackson immunoresearch, West Grove, Pa., USA) for full antibodies or anti-rabbit conjugated to alkaline phosphatase (Sigma-Aldrich, St. Louis, Mo., USA) for serum ELISA. Detection of HRP conjugates was achieved with 3,3',5,5'-tetramethybenzidine (TMB/E, Millipore, Billerica, Mass., USA) while detection of alkaline phosphatase conjugates was achieved with SIGMAFAST p-nitrophenyl phosphate tablets (Sigma-Aldrich, St. Louis, Mo., USA).

Capture ELISA: Maxisorp 96-well microtiter plate (Nunc, Sigma-Aldrich, St. Louis, Mo., USA) was coated overnight (50 µL/well) with 2 µg/ml TL1 antibody in Carbonate bicarbonate buffer. Washing and blocking were carried out as described above. Live Schu S4 bacteria were diluted in PBS and added at different concentrations to the plates for a one-hour incubation; the plates were then washed with PBST and incubated with HRP conjugated T5 (Mechaly et al 2016). The rest of the steps were as described for direct ELISA.

Nucleic Acid Analysis

Phagemid DNA was isolated using the QIAprep spin Miniprep kit (Qiagen, GmbH, Hilden, Germany), and scFvs were sequenced by the ABI Prism 310 Genetic Analyzer (Applied Biosystems, Foster City, Calif., USA) using primers TAB-RI and CBD-AS (Noy-Porat et al. 2016). Nucleic acids sequences of the VH and VL fragments were compared to the rabbit germline immunoglobulin genes by using the IgBlast tool (http://www.ncbi.nlm.nih.gov/igblast/).

Production of Full-Length Antibodies

Phagemid DNA of the TL1 antibody clone was isolated using QIAprep spin Miniprep kit (Qiagen, GmbH, Hilden, Germany), and VH and VL sequences were cloned into a mammalian full-length immunoglobulin expression vector (Rosenfeld et al 2009), providing each chain with the corresponding human constant genes and resulting in IgG1/K chimeric rabbit-human antibody expression. FreeStyle Max 293 cells (Thermo Scientific, Waltham, Mass., USA) were transiently transfected with the vector, and after a week, the supernatant was collected and the antibodies were purified on a HiTrap Protein-A column (GE healthcare, Little Chalfont, UK).

Antibody Labeling

Biotinylation of the purified IgG antibody was carried out using sulfo-NHS-SS-biotin [sulfosuccinimidyl-2-(biotinamido) ethyl-1,3-dithiopropionate; Pierce 21331] according to the manufacturer's instructions.

Alkaline-phosphatase labeling of antibodies was carried out using the Lightning-link alkaline phosphatase conjugation kit (Innova Biosciences, UK).

Conjugation of TL1 to Alexa488 was carried out using a commercial kit (A10235, Thermo fisher Scientific, Walthman, Mass., USA, 02451) according to the manufacturer's instruction.

Construction and Purification of Soluble scFv TL

The pET SUMO plasmid, part of the Champion™ pET SUMO protein expression system (Invitrogen K300-01), was used for cloning of TL1-scFv antibody for soluble expression. The scFv was amplified from phagemid DNA and cloned into linearized pET SUMO using A/T ligation. The plasmid was freshly transformed to *E. coli* BL21 (DE3)

(Novagen 713974) and expression was carried out in Terrific Broth medium supplemented with 1% glucose and 50 µg/mL Kanamycin at 37° C., 250 rpm. When the suspension reached an $OD_{600}$ of 07-0.9, IPTG was added to a final concentration of 0.5 mM and the temperature was lowered to 25° C. After an O.N growth the cells were harvested, re-suspended in 20 mM phosphate buffer pH 7.4 (supplemented with 0.5M NaCl, 20 mM Imidazole and Protease inhibitors; Sigma-Aldrich, St. Louis, Mo., USA) and sonicated under ice. After sonication, the suspension was precipitated (9500 g, 20 minutes, 4° C.) and Benzonase nuclease (Sigma-Aldrich, St. Louis, Mo., USA) was added to a final concentration of 50 units/mL to the supernatant. The supernatant was then filtered (45 µm) and the SUMO-scFv was purified on a HisTrap column (GE 17-5447-01) according to the manufacturer's instructions. The buffer of the purified antibody was exchanged to PBS using a 10Kd Amicon ultra (Millipore UFC901024).

Binding Studies

Binding studies were carried out using the Octet Red system (ForteBio, Version 8.1, Menlo Park, Calif., USA, 2015) that measures biolayer interferometry (BLI). All steps were performed at 30° C. with shaking at 1500 rpm in a black 96-well plate containing 200 µL solution in each well. Streptavidin-coated biosensors were loaded with biotinylated antibody (5 µg/mL) for 300 s followed by a wash step. The sensors were then reacted for 300 s with increasing concentrations of LVS bacteria or LPS extract (Phillips et al 2004) and then moved to buffer-containing wells for another 300 s (dissociation phase). Binding and dissociation were measured as changes over time in light interference after subtraction of parallel measurements from unloaded biosensors. Sensorgrams were fitted with a 1:1 binding model using the Octet data analysis software 8.1 (Fortebio, Menlo Park, Calif., USA, 2015), and the presented values are an average of several repeated measurements.

Western Blot

To obtain bacteria lysate, inactivated bacteria was boiled for 10 min with 4×Laemmli sample buffer (Bio-Rad, USA). Bacterial lysates, LPS and protein markers (Precision Plus protein standards dual color, Bio-Rad, USA) were resolved on NuPAGE 4-12% Bis-Tris gel 1.5 mm×10 well (Invitrogen NP0335). Gels were blotted on a nitrocellulose filter (iBlot NC gel transfer stacks, Mini; Invitrogen, USA) and blocked for 1 hour in Odyssey blocking buffer (Li-Cor, USA). The nitrocellulose filters were then washed 3 times in wash solution (1% 10 mM Tris 1M pH 8, 3% NaCl 5M, 0.05% Tween20 in 1 liter $dH_2O$) and then probed (4° C., O.N) with T5 or TL1 that were diluted in incubation buffer (5% nonfat dry milk; Bio-Rad, USA). The nitrocellulose filters were then washed 3 times in wash solution. T5 was detected with Goat anti rabbit IRDye 800CW (Li-Cor, USA) diluted 1:20,000 in incubation buffer. TL1 was detected with Goat anti human IRDye 800CW (Li-Cor, USA) diluted 1:20,000 in incubation buffer. After another extensive wash step the filters were developed in ODYSSEY CLx (Li-Cor, USA).

IFA

IFA was carried out with LVS bacteria ($1 \times 10^8$ cfu/ml) air dried on a multispot slide. The slide was incubated for 30 min (37° C., humid incubator) with Alexa 488 conjugated TL, diluted to a final concentration of 1 µg/ml in assay buffer (PBS supplemented with 2% BSA and 0.05% tween20). Following incubation the slide was rinsed with water and dried. The slide was than examined under fluorescent illumination with a Nikon phase microscope (Nikon eclipse E400).

Macrophage Infection Assay

J774A.1 macrophages were seeded at $2 \times 10^4$ cells/well in white 96 well plates (Corning, Corning, N.Y.), and allowed to adhere overnight. On the next day, logarithmic phase LVS-pXB173-lux bacteria were washed twice with PBS and incubated with 0.2, 2, 20 or 200 nM of TL1 or scFv-TL1 for 1 hour at room temperature. Bacteria were added to the macrophages at an MOI (multiplicity of infection) of 1, and the plate was then centrifuged at 1000 rpm for 5 minutes. After 1 hour incubation at 37° C. in a humidified 5% CO2 incubator, cells were washed twice with PBS, and gentamycin (2 µg/ml) was added to the growth medium for 24 hours, after which the luminescence level was evaluated using the Victor3 (Perkin Elmer) luminometer.

For the confocal microscopy, J774A.1 cells were seeded on 8-well chamber slides (ibidi, Martinsried, Germany) at $1 \times 10^5$ cells/well, and allowed to adhere overnight. Cells were then infected as described above for 2 hours, washed three times with PBS and fixed in ice-cold 100% methanol for 2 minutes. Cells were blocked in PBS+2% BSA+2% naïve rabbit serum for 20 minutes in 37° C. Bacteria were stained using an Alexa 488-conjugated rabbit anti-*F. tularensis* serum (1:200). Cell nuclei were stained with DAPI (11 µg/ml, Sigma-Aldrich, St. Louis, Mo., USA). Samples were viewed using a Zeiss LSM710 confocal microscope (Zeiss, Oberkochen, Germany).

Example 1

Immunization and Characterization of the Antibody Response

In order to generate antibodies which are highly specific towards the Ft LPS moiety, a rabbit immunization process took place using live bacteria. The immunization protocol involved repeated exposures of rabbits to LVS, in order to elicit a strong immune response. To this end, a rabbit was infected with three successive injections of $1\times10^8$ CFU LVS and the elicited titer against the whole bacteria was evaluated (FIG. 1A). Interestingly, the antibody titer continued to increase within the following 40 days post the last dose, thus raising the possibility that LVS was still present at that time point. To further increase the anti-LVS titer, the animal was exposed to two additional successive high doses of LVS ($1\times10^9$ CFU) until a plateau was reached.

To evaluate the pattern of the elicited antibody towards *F. tularensis*, a Western blot analysis was performed using bacterial lysates (FIG. 1B). The resulted binding-pattern indicated that indeed antibodies were raised against the LPS moiety (characterized by the ladder pattern as also seen with the binding of the purified LPS preparation) and against several bacterial proteins. To further confirm these findings, the antibodies were reacted with LVS-S lysate, a phase variation of Ft that has an impaired O-antigen (also known as LVS gray variant). As expected, the antibody binding pattern lacked the characteristic LPS ladder while they do bind to the bacterial proteins (FIG. 1B). Importantly, similar binding-pattern was observed toward SchuS4 extracts.

Example 2

Isolation and Characterization of Anti-LPS High Affinity Antibody

A scFv phage-display library was constructed from cDNA templates derived from RNA isolated from the lymphatic organs and peripheral blood of the LVS-immunized rabbit. A set of degenerate primers was designed to amplify the rabbit VH/VL genes immunoglobulin families (Mechaly et al. 2018). A total of 16 forward and 7 reverse primers were designed, giving 56 different primer pairs to amplify rabbit VH and Vκ sequences. For example, a specific primer set used to amplify the TL1 antibody included the primer termed "VH-For", having the nucleic acid sequence CAGTCGTTGGAGGAGTCC, denoted by SEQ ID NO. 11 (the forward primer used for amplifying the variable heavy chain), the primer termed "VH-Rev", having the nucleic acid sequence TGAAGAGACGGTGAC, denoted by SEQ ID NO. 12 (the reverse primer used for amplifying the variable heavy chain), the primer termed "VL-For", having the nucleic acid sequence GATGTCGTTTATGACCC, denoted by SEQ ID NO. 13 (the forward primer used for amplifying the variable light chain) and the primer termed "VL-Rev", having the nucleic acid sequence TTTCGACGACCACCTCGG, denoted by SEQ ID NO. 14 (the reverse primer used for amplifying the variable light chain).

The VH and Vκ gene pools were assembled by PCR to obtain combinatorial scFv fragments that were inserted into a phagemid vector to create a large, diverse phage-display library. The library was subjected to three rounds of panning using a plate-coated LVS bacteria and by the end of the panning process, individual clones were screened by direct phage-ELISA for their ability to bind LVS. It was found that 80% of the colonies reacted with LVS, and were all found to possess the same VH-VL sequence.

Figure 2A:
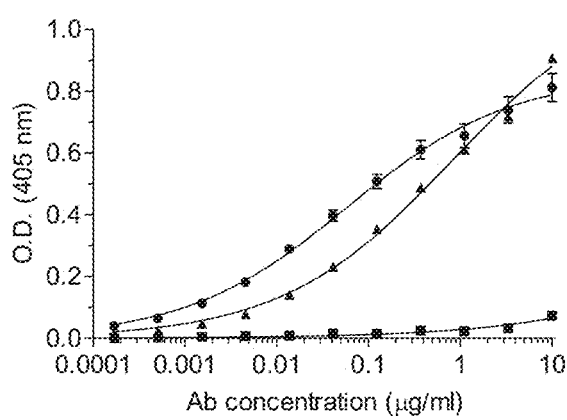
FIG. 2A is a graph showing the reactivity profile of the TL1 antibody as determined by ELISA using either LVS (circles), SchuS4 (triangles) or LVS-S(squares) as the coated layer. The X axis represents antibody (Ab) concentration (µg/ml) and the Y axis represents level of absorption at O.D. 405. Points are the mean±STD of quadruplicates.
Figure 2B:
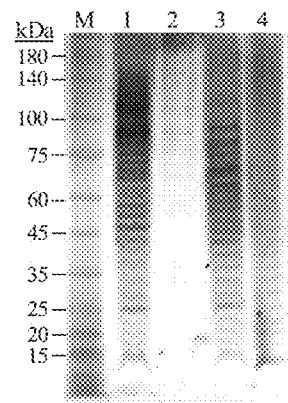
FIG. 2B shows Western blot analysis of TL1. M—Protein size marker, 1—LVS lysate; 2—LVS-S lysate; 3—SchuS4 lysate; 4—purified LPS of LVS.

To enable further characterization, the isolated scFv-displayed antibody was reformatted and expressed as a chimeric antibody (Rosenfeld et al. 2009, Noy-Porat et al. 2016) composed of rabbit variable chains and human constant regions (IgG1/κ). The novel antibody, termed TL1 was expressed in cultured cells and then further characterized for its ability to bind the target bacteria. Using ELISA, it was found that TL1 binds to both LVS and SchuS4 with high affinity, while it does not binds to the LVS-S strain (FIG. 2A), suggesting that it is specific to the Ft OAg. Western blot analysis also confirmed that observation, where TL1 reacted solely with LVS, SchuS4 or purified LPS (FIG. 2B). Moreover, the binding pattern of TL indicates that it binds strongly to the longer chains of the LPS ladder, thus suggesting that its antigenic moiety is the four-sugar repeats in the LPS OAg chains (Roche et al. 2011). This is in contrast to the binding pattern of antibodies directed against either the single non-reducing end or the single reducing end of the OAg chain. The specificity of this antibody toward Ft was further confirmed using binding assay against other gram-negative bacteria (including *Y. pestis* and *salmonella*) and was found to be highly specific.

Figure 2C:
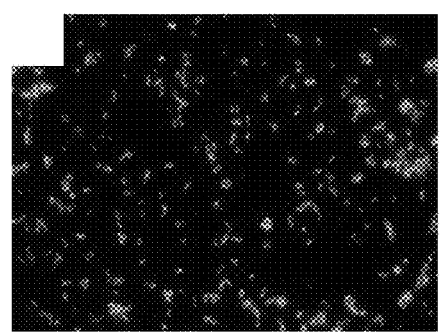
FIG. 2C is a photomicrograph showing immunofluorescence staining of LVS using Alexa 488-conjugated TL1.

The binding of TL to LVS was further analyzed by immunofluorescence assay (IFA), where it exhibited the LPS characteristic staining as would be expected from an anti-LPS antibody (FIG. 2C).

Figure 3A:
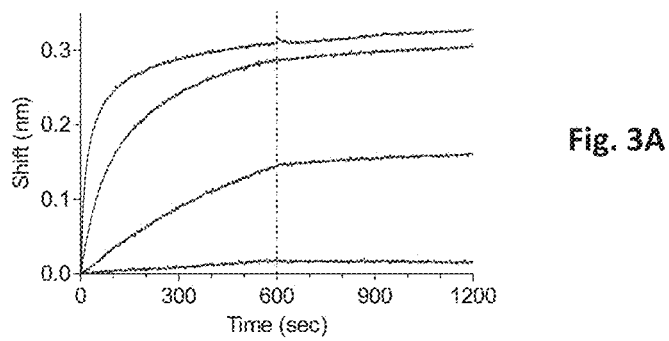
FIG. 3A & FIG. 3B is a graph showing changes over time in light interference after subtraction of parallel measurements from reference biosensor (Shift (nm)) as a function of time (sec). Biotinylated TL1 was immobilized on streptavidin-biosensors and reacted for 600 s with increasing concentrations of (FIG. 3A) LVS (from bottom up: $1\times10^6$, $1\times10^7$, $1\times10^8$ and $1\times10^9$ CFU/ml), or (FIG. 3B) purified LPS (from bottom up: 0.2, 1 and 5 big/ml). The sensors were then immersed in buffer for another 600 s (marked by dashed line).

To further characterize the binding of TL to Ft, the Octet Red biolayer interferometry system was used. To this end, TL1 was biotinylated, immobilized on the Octet sensor and monitored for its binding profile with different concentrations of LVS revealing a positive dose response where at higher LVS concentrations a faster association and saturation was achieved (FIG. 3A). Accurate determination of antibody affinity requires the interaction of the antibody with several concentrations of the antigen. Due to the repetitive nature of the target antigen of TL1, it is impossible to calculate its concentration and therefore the association constant ($k_{on}$) could not be determined. On the other hand, the dissociation constant ($k_{off}$) does not require prior knowledge of the antigen concentrations and therefore it can be calculated. It was found that the dissociation rate was extremely slow (below the Octet Red detection limit, $1 \times 10^{-7}$ $s^{-1}$) and could not be measured even when the dissociation phase was monitored for longer periods, indicating that TL exhibits ultra-high affinity value that is in the sub-pM range. Moreover, even upon exposing the LVS-TL1 complex to a highly acidic environment (pH 2.7), no dissociation could be observed.

Figure 3B:
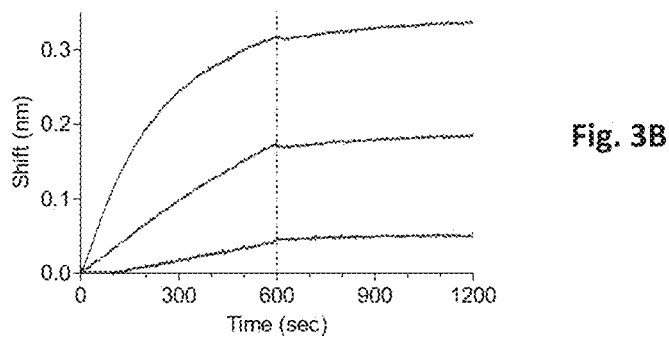

To further strengthen this observation, the binding assay was repeated using several concentrations of purified LPS (the exact molarity cannot be determined due to the high variability of the LPS chains length within the sample) and indeed, a similar binding pattern was observed and no dissociation could be determined (FIG. 3B).

Example 3

Sensitive Detection of *F. tularensis*

Figure 4:
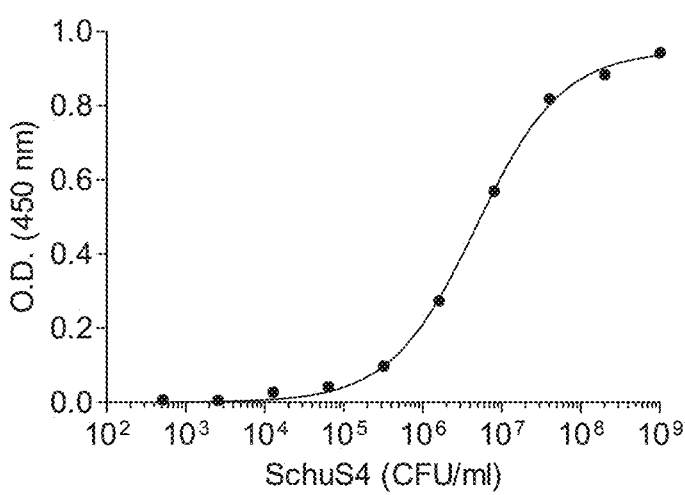
FIG. 4 is a graph showing detection of Ft by ELISA. Binding of SchuS4 to TL1-coated wells is demonstrated by O.D. (450 nm) reading as a function of increasing concentrations of SchuS4 (CFU/ml). Points are average±STD fitted by non-linear regression.

In light of the very high affinity and specificity of the TL1 antibody towards Ft, its activity in a detection assay of the virulent SchuS4 was also assessed. Thus, TL1 was immobilized on ELISA plates to serve as the capture moiety, incubated for one hour with increasing concentrations ($10^2$-$10^9$ CFU/ml) of SchuS4. The IgG fraction of anti-*F. tularensis* hyper-immune rabbit sera (termed T5) served as the detection component. The plates were then washed, and alkaline-phosphatase labeled anti-Ft IgG antibodies were added. Indeed, a sigmoidal dose response curve was generated with an estimated limit of detection (LOD) of $1 \times 10^4$ CFU/ml (FIG. 4). Apparently, the assay exhibited very high sensitivity of Ft detection.

Example 4

Binding of TL1-scFv Inhibits *F. tularensis* Uptake by Macrophages

In the following example, the ability of the anti Ft-LPS monoclonal antibodies to affect the uptake of Ft by macrophages was assessed. The experimental setup included cultured J774A.1 murine macrophages that were incubated with LVS-pXB173-lux (MOI=1) in the absence or presence of TL1. The cells were lysed 24 hours later and the intracellular luminescence levels were determined. Incubation of LVS in the presence of TL1 (0.2 and 2 nM) significantly enhanced their uptake by 13-16 fold (FIG. 5A). Interestingly, at higher concentrations of TL1 the bacterial uptake level dramatically declined in an antibody-dose dependent manner (to 6 and 4-fold over control at 20 and 200 nM of TL1, respectively). Without wishing to be bound by theory, the fact that at higher concentrations the binding of antibodies to Ft-LPS may interfere with the phagocytosis process suggests that two mechanisms co-exist (uptake-enhancement versus uptake-inhibition). It was therefore of interest to test the direct effect of antibody-binding to Ft-LPS on bacterial uptake, while eliminating the FcγR mediated uptake.

Accordingly, a soluble single-chain fragment (scFv) of TL1 (TL1-scFv) was created. The TL1-scFv comprises the VH-VL regions of the antibody and lacks the Fc region. Binding studies using octet revealed that the TL1-scFv retained its affinity towards Ft (exhibiting the same binding pattern as the IgG format). Next, cultured macrophages were incubated with LVS-pXB173-lux in the presence of increasing concentrations of TL1-scFv and bacterial uptake was measured 24 hours later. In the presence of 0.2 and 2 nM of TL1-scFv, there is no significant change in the amount of bacterial uptake when compared to control (FIG. 5B). However, increasing the TL1-scFv concentrations to 20 and 200 nM dramatically affected the bacterial uptake, where at 200 nM this process was inhibited by 70%.

In order to verify that the observed inhibitory effect of TL1-scFv is on the direct interactions of LVS with the macrophages and not due to its inability to multiply intracellularly, qualitative confocal microscopy was used. To this end, murine macrophages were incubated with LVS and either TL1 or TL1-scFv for a short incubation period (2 hours) followed by washing, fixation and imaging using polyclonal anti-LVS antibodies (Alexa 488-conjugated rabbit anti-*F. tularensis* antibodies). In addition, cell nuclei were stained with DAPI. Indeed, only in the presence of TL1 there is an increase of macrophages-containing bacteria (FIG. 5C-E).

The invention claimed is:

1. An isolated monoclonal antibody or antigen-binding fragment thereof which binds to *Francisella tularensis* LPS, wherein said antibody comprises a heavy chain complementarity determining region (CDRH) 1 denoted by SEQ ID NO. 5, CDRH2 denoted by SEQ ID NO. 6, CDRH3 denoted by SEQ ID NO. 7, and the light chain complementarity determining region (CDRL) 1 denoted by SEQ ID NO. 8, a CDRL2 denoted by SEQ ID NO. 9, and a CDRL3 denoted by SEQ ID NO. 10.

2. The isolated monoclonal antibody according to claim 1, wherein said antibody comprises a heavy chain variable region and a light chain variable region, wherein said heavy chain variable region is encoded by a nucleic acid sequence which is at least 70% identical to the nucleic acid sequence denoted by SEQ ID NO. 1 and wherein said light chain variable region is encoded by a nucleic acid sequence which is at least 70% identical to SEQ ID NO. 2.

3. The isolated monoclonal antibody according to claim 1, wherein said antibody comprises a heavy chain variable region comprising the amino acid sequence denoted by SEQ ID NO. 3 or a variant thereof and a light chain variable region comprising the amino acid sequence denoted by SEQ ID NO. 4, or a variant thereof.

4. An isolated nucleic acid molecule comprising a nucleotide sequence encoding the isolated monoclonal antibody or antigen-binding fragment thereof of claim 1 or an isolated monoclonal antibody or an antigen binding fragment thereof comprising a heavy chain variable region comprising the amino acid sequence denoted by SEQ ID NO:3 and a light chain variable region comprising the amino acid sequence denoted by SEQ ID NO:4.

5. An expression vector comprising the isolated nucleic acid molecule according to claim 4.

6. A host cell transfected with the expression vector according to claim 5.

7. A kit for detecting *Francisella tularensis* infection comprising:
   a. at least one isolated monoclonal antibody or antigen-binding fragment thereof according to claim 1;
   b. means for detection of said isolated monoclonal antibody; and optionally
   c. instructions for use of said kit.

8. A pharmaceutical composition, comprising, as an active ingredient, the isolated monoclonal antibody or antigen-binding fragment thereof according to claim 1, and a pharmaceutically acceptable carrier, excipient or diluent.

* * * * *

SEQUENCE LISTING

<160> NUMBER OF SEQ ID NOS: 14

<210> SEQ ID NO 1
<211> LENGTH: 360
<212> TYPE: DNA
<213> ORGANISM: Oryctolagus cuniculus
<220> FEATURE:
<221> NAME/KEY: misc_feature
<223> OTHER INFORMATION: Heavy chain nucleic acid sequence

<400> SEQUENCE: 1
cagtcgttgg aggagtccgg gggagacctg gtcaaacctg gggcatccct gacactcacc 60
tgcacagcct ctggattcac cctcagtagc tactggattt cctgggtccg ccaggctcca 120
gggaaggggc tggagtggat cgcatcgttt agtacttttt atgaaaatgg aaattacgcg 180
gactgggcga aaggccgatt caccgtctcc aaatcctcgt cgaccacggt gactctgcaa 240
atgaccagtc tgacagccgc ggacacggcc acctatttct gtgggagagg ggagtatatt 300
aatgataatg attttccata caggttgtgg ggcccaggca ccctggtcac cgtctcttca 360

<210> SEQ ID NO 2
<211> LENGTH: 330
<212> TYPE: DNA
<213> ORGANISM: Oryctolagus cuniculus
<220> FEATURE:
<221> NAME/KEY: misc_feature
<223> OTHER INFORMATION: Light chain nucleic acid sequence

<400> SEQUENCE: 2
gatgtcgtta tgacccagac tccagcctcc gtgtctgcag ctgtgggagg cacagtcacc 60
atcaagtgcc aggccagtga gagcattaat agtagattag cctggtatca gcagaaacga 120
gggcagcgtc ccaagctcct gatctattct gcatccactc tggaatctgg ggtcccatcg 180
cggttcaagg gcagtggatc tgggacagag tacactctca ccatcagcga cctggagtgt 240
gccgatgctg ccacttacta ctgtcaaacc tattatgata gtggtagtag tgctaatgat 300
ttcggcggag ggaccgaggt ggtcgtcgaa 330

<210> SEQ ID NO 3
<211> LENGTH: 120
<212> TYPE: PRT
<213> ORGANISM: Oryctolagus cuniculus
<220> FEATURE:
<221> NAME/KEY: MISC_FEATURE
<223> OTHER INFORMATION: Heavy chain amino acid sequence

<400> SEQUENCE: 3

Gln Ser Leu Glu Glu Ser Gly Gly Asp Leu Val Lys Pro Gly Ala Ser
1 5 10 15

Leu Thr Leu Thr Cys Thr Ala Ser Gly Phe Thr Leu Ser Ser Tyr Trp
20 25 30

Ile Ser Trp Val Arg Gln Ala Pro Gly Lys Gly Leu Glu Trp Ile Ala
35 40 45

```
Ser Phe Ser Thr Phe Tyr Glu Asn Gly Asn Tyr Ala Asp Trp Ala Lys
    50                  55                  60

Gly Arg Phe Thr Val Ser Lys Ser Ser Thr Val Thr Leu Gln
 65              70                  75                  80

Met Thr Ser Leu Thr Ala Ala Asp Thr Ala Thr Tyr Phe Cys Gly Arg
                 85                  90                  95

Gly Glu Tyr Ile Asn Asp Asn Asp Phe Pro Tyr Arg Leu Trp Gly Pro
                100                 105                 110

Gly Thr Leu Val Thr Val Ser Ser
            115                 120

<210> SEQ ID NO 4
<211> LENGTH: 110
<212> TYPE: PRT
<213> ORGANISM: Oryctolagus cuniculus
<220> FEATURE:
<221> NAME/KEY: MISC_FEATURE
<223> OTHER INFORMATION: Light chain amino acid sequence

<400> SEQUENCE: 4

Asp Val Val Met Thr Gln Thr Pro Ala Ser Val Ser Ala Ala Val Gly
  1               5                  10                  15

Gly Thr Val Thr Ile Lys Cys Gln Ala Ser Glu Ser Ile Asn Ser Arg
                 20                  25                  30

Leu Ala Trp Tyr Gln Gln Lys Arg Gly Gln Arg Pro Lys Leu Leu Ile
             35                  40                  45

Tyr Ser Ala Ser Thr Leu Glu Ser Gly Val Pro Ser Arg Phe Lys Gly
     50                  55                  60

Ser Gly Ser Gly Thr Glu Tyr Thr Leu Thr Ile Ser Asp Leu Glu Cys
 65              70                  75                  80

Ala Asp Ala Ala Thr Tyr Tyr Cys Gln Thr Tyr Tyr Asp Ser Gly Ser
                 85                  90                  95

Ser Ala Asn Asp Phe Gly Gly Gly Thr Glu Val Val Val Glu
                100                 105                 110

<210> SEQ ID NO 5
<211> LENGTH: 5
<212> TYPE: PRT
<213> ORGANISM: Oryctolagus cuniculus
<220> FEATURE:
<221> NAME/KEY: MISC_FEATURE
<223> OTHER INFORMATION: Heavy chain CDRH1

<400> SEQUENCE: 5

Ser Tyr Trp Ile Ser
  1               5

<210> SEQ ID NO 6
<211> LENGTH: 17
<212> TYPE: PRT
<213> ORGANISM: Oryctolagus cuniculus
<220> FEATURE:
<221> NAME/KEY: MISC_FEATURE
<223> OTHER INFORMATION: Heavy chain CDRH2

<400> SEQUENCE: 6

Ser Phe Ser Thr Phe Tyr Glu Asn Gly Asn Tyr Ala Asp Trp Ala Lys
  1               5                  10                  15

Gly

<210> SEQ ID NO 7
```

```
<211> LENGTH: 13
<212> TYPE: PRT
<213> ORGANISM: Oryctolagus cuniculus
<220> FEATURE:
<221> NAME/KEY: MISC_FEATURE
<223> OTHER INFORMATION: Heavy chain CDRH3

<400> SEQUENCE: 7

Gly Glu Tyr Ile Asn Asp Asn Asp Phe Pro Tyr Arg Leu
1               5                   10

<210> SEQ ID NO 8
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: Light chain CDRH1

<400> SEQUENCE: 8

Gln Ala Ser Glu Ser Ile Asn Ser Arg Leu Ala
1               5                   10

<210> SEQ ID NO 9
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: Light chain CDRH2

<400> SEQUENCE: 9

Ser Ala Ser Thr Leu Glu Ser
1               5

<210> SEQ ID NO 10
<211> LENGTH: 12
<212> TYPE: PRT
<213> ORGANISM: Oryctolagus cuniculus
<220> FEATURE:
<221> NAME/KEY: MISC_FEATURE
<223> OTHER INFORMATION: Light chain CDRH3

<400> SEQUENCE: 10

Gln Thr Tyr Tyr Asp Ser Gly Ser Ser Ala Asn Asp
1               5                   10

<210> SEQ ID NO 11
<211> LENGTH: 18
<212> TYPE: DNA
<213> ORGANISM: Artificial Sequence
<220> FEATURE:
<223> OTHER INFORMATION: VH-For primer

<400> SEQUENCE: 11
cagtcgttgg aggagtcc                                                 18

<210> SEQ ID NO 12
<211> LENGTH: 15
<212> TYPE: DNA
<213> ORGANISM: Artificial Sequence
<220> FEATURE:
<223> OTHER INFORMATION: VH-Rev primer

<400> SEQUENCE: 12
tgaagagacg gtgac                                                    15
```

```
<210> SEQ ID NO 13
<211> LENGTH: 16
<212> TYPE: DNA
<213> ORGANISM: Artificial Sequence
<220> FEATURE:
<223> OTHER INFORMATION: VL-For primer

<400> SEQUENCE: 13
gatgtcgtta tgaccc                                                       16

<210> SEQ ID NO 14
<211> LENGTH: 17
<212> TYPE: DNA
<213> ORGANISM: Artificial Sequence
<220> FEATURE:
<223> OTHER INFORMATION: VL-Rev primer

<400> SEQUENCE: 14
ttcgacgacc acctcgg                                                      17
```